(12) United States Patent
Kaneko

(10) Patent No.: US 10,908,167 B2
(45) Date of Patent: Feb. 2, 2021

(54) MASS SPECTROMETRY METHOD FOR POLYPEPTIDES

(71) Applicant: SHIMADZU CORPORATION, Kyoto (JP)

(72) Inventor: Naoki Kaneko, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 201 days.

(21) Appl. No.: 15/209,331

(22) Filed: Jul. 13, 2016

(65) Prior Publication Data

US 2017/0016910 A1 Jan. 19, 2017

(30) Foreign Application Priority Data

Jul. 14, 2015 (JP) ................................. 2015-140899

(51) Int. Cl.
*G01N 33/68* (2006.01)

(52) U.S. Cl.
CPC . *G01N 33/6851* (2013.01); *G01N 2333/4709* (2013.01)

(58) Field of Classification Search
CPC .................. G01N 2333/4709; G01N 33/6851
See application file for complete search history.

(56) References Cited

U.S. PATENT DOCUMENTS

2016/0334420 A1* 11/2016 Kaneko .............. G01N 33/6896

OTHER PUBLICATIONS

Kaneko et al., "Identification and quantification of amyloid beta-related peptides in human plasma using matrix-assisted laser desorption/ionization time-of-flight mass spectrometry," Proc. Jpn. Acad. Ser. B Phys. Biol. Sci., 2014, vol. 90, No. 3 (March), pp. 104-117.*
Sun et al., "N-glycans and the N terminus of protein C inhibitor affect the cofactor-enhanced rates of thrombin inhibition," J. Biol. Chem., 2008, vol. 283, pp. 18601-18611.*
A printout retrieved from https://www.thermofisher.com/order/catalog/product/89902 on Jul. 27, 2018.*
Beima et al., "T-bet Binding to Newly Identified Target Gene Promoters Is Cell Type-independent but Results in Variable Context-dependent Functional Effects," J. Biol. Chem., 2006, vol. 281, No. 17, pp. 11992-12000.*
Wang, Rong, et al.; "The Profile of Soluble Amyloid β Protein in Cultured Cell Media—Detection and Quantification of Amyloid β Protein and Variants by Immunoprecipitation-Mass Spectrometry"; The Journal of Biological Chemistry, 271(50): 31894-31902 (Dec. 1996).
Portelius, Erik, et al.; "Characterization of Amyloid R Peptides in Cerebrospinal Fluid by an Automated Immunoprecipitation Procedure Followed by Mass Spectrometry"; Journal of Proteome Research, 6: 4433-4439 (2007); published on Web Oct. 10, 2007.
Pannee, Josef, et al.; "The amyloid-β degradation pattern in plasma—A possible tool for clinical trials in Alzhemier's disease"; Neuroscience Letters, 573: 7-12 (2014).
Nittis, Thalia, et al.; Revealing Novel Telomere Proteins Using in Vivo Cross-linking, Tandem Affinity Purification, and Label-free Quantitative LC-FTICR-MS; Molecular & Cellular Proteomics, 9: 1144-1156 (Jan. 2010).

* cited by examiner

*Primary Examiner* — Galina M. Yakoleva
(74) *Attorney, Agent, or Firm* — Morgan, Lewis & Bockius LLP

(57) ABSTRACT

Provided is a method for measuring a target polypeptide in a biological sample abundantly containing impurities by mass spectrometry. A method for measuring a target polypeptide in a biological sample includes: a first reaction step of bringing a liquid containing a biological sample into contact with a first antibody-immobilizing carrier to bind the target polypeptide in the biological sample with the first carrier; a first washing step of washing the first carrier; a first eluting step of eluting the target polypeptide from the first carrier by using an acidic solution to obtain a first eluate; a neutralizing step of obtaining a first purified solution by adding a neutral buffer to the first eluate; a second reaction step of bringing the first purified solution into contact with a second antibody-immobilizing carrier, to bind the target polypeptide in the first purified solution with the second carrier; a second washing step of washing the second carrier; a second eluting step of eluting the target polypeptide from the second carrier by using an acidic solution to obtain a second purified solution; and a step of detecting the target polypeptide in the second purified solution by mass spectrometry.

21 Claims, 7 Drawing Sheets

Specification includes a Sequence Listing.

SEQUENCE LISTING

<160> NUMBER OF SEQ ID NOS: 5

<210> SEQ ID NO 1
<211> LENGTH: 38
<212> TYPE: PRT
<213> ORGANISM: Homo Sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
        35

<210> SEQ ID NO 2
<211> LENGTH: 38
<212> TYPE: PRT
<213> ORGANISM: Homo Sapiens

<400> SEQUENCE: 2

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 3
<211> LENGTH: 40

-continued

```
<212> TYPE: PRT
<213> ORGANISM: Homo Sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 4
<211> LENGTH: 42
<212> TYPE: PRT
<213> ORGANISM: Homo Sapiens

<400> SEQUENCE: 4

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 5
<211> LENGTH: 43
<212> TYPE: PRT
<213> ORGANISM: Homo Sapiens

<400> SEQUENCE: 5

Val Lys Met Asp Ala Glu Phe Arg His Asp Ser Gly Tyr Glu Val His
1               5                   10                  15

His Gln Lys Leu Val Phe Phe Ala Glu Asp Val Gly Ser Asn Lys Gly
            20                  25                  30

Ala Ile Ile Gly Leu Met Val Gly Gly Val Val
        35                  40
```

MASS SPECTROMETRY METHOD FOR POLYPEPTIDES

TECHNICAL FIELD

The present invention pertains to the clinical medicine field, the analytical chemistry field, and the biological research field, and relates to a method for measuring polypeptides by mass spectroscopy. More specifically, the present invention relates to a method for measuring target trace polypeptides in a biological sample abundantly containing impurities by mass spectrometry, with high selectivity by consecutive affinity purification.

BACKGROUND ART

As a pretreatment for mass spectrometric measurement of trace polypeptides (peptide and protein) in a sample, affinity purification such as immunoprecipitation is often employed. In Non-patent Documents 1, 2, for mass spectrometric measurement of amyloid β protein (Aβ) in a supernatant of culture cells or in cerebrospinal fluid, anti-Aβ antibodies are immobilized to Protein G beads or anti-mouse IgG antibody beads to prepare antibody-immobilizing beads, and immunoprecipitation is conducted by using the antibody-immobilizing beads. With this method, although Aβ in a supernatant of culture cells or in cerebrospinal fluid containing relatively small quantities of impurity substances can be measured by mass spectrometry, it is difficult to conduct such measurement in plasma or serum abundantly containing impurity substances because large quantities of impurity substances remain on the antibody-immobilizing beads due to non-specific adsorption. When impurity substances are abundantly contained, ionization of the polypeptide to be measured is suppressed in the mass spectrometry.

In Non-patent Document 3, for the purpose of removing impurity substances, a step of bringing plasma into contact with Protein G beads for 1 hour is repeated twice before affinity purification, to reduce the impurity substances, and thus the sensitivity of mass spectrometry is improved. However, impurity peaks are still detected. Further, since this method requires using as much as 5 mL of plasma, general-purpose properties for use in researches and disease examinations is poor. It is necessary to further increase the sensitivity so as to be detected with a small amount of sample.

In order to reduce non-specifically adsorbed impurity substances, Tandem Affinity Purification (TAP) is sometimes used. In Non-patent Document 4, HA-FLAG-TIN2, which is prepared by fusing two kinds of tags FLAG and HE to protein TIN2 by genetic engineering techniques, is expressed in culture cells, and TAP is used for the lysate of the cells. In this technique, contamination with impurity substances is reduced by conducting consecutive affinity purification with the use of two antibody-immobilizing carriers including an anti-FLAG antibody-immobilizing carrier and an anti-HA antibody-immobilizing carrier. In this technique, the effect of reducing non-specifically adsorbed substances is achieved by the two kinds of antibodies; however, the technique requires fusing FLAG and HE to a target protein in a genetic engineering manner, and thus is not applicable to a biological sample such as plasma or serum for which an genetic engineering operation cannot be made. Also, in the eluting step in the immunoprecipitation using the anti-FLAG antibody-immobilizing carrier, the elution efficiency is poor because HA-FLAG-TIN2 is eluted with FLAG peptide, and thus it is not possible to recover the captured target protein satisfactorily.

PRIOR ART DOCUMENT

Non-Patent Documents

Non-Patent Document 1: Wang R, Sweeney D, Gandy S E, Sisodia S S.: The profile of soluble amyloid beta protein in cultured cell media. Detection and quantification of amyloid beta protein and variants by immunoprecipitation-mass spectrometry. J Biol Chem. 1996; 271(50): 31894-902

Non-Patent Document 2: Portelius E, Tran A J, Andreasson U, Persson R, Brinkmalm G, Zetterberg H, Blennow K, Westman-Brinkmalm A.: Characterization of amyloid beta peptides in cerebrospinal fluid by an automated immunoprecipitation procedure followed by mass spectrometry. J Proteome Res. 2007; 6(1):4433-9

Non-Patent Document 3: Pannee J, Törnqvist U, Westerlund A, Ingelsson M, Lannfelt L, Brinkmalm G, Persson R, Gobom J, Svensson J, Johansson P, Zetterberg H, Blennow K, Portelius E.: The amyloid-β degradation pattern in plasma—a possible tool for clinical trials in Alzheimer's disease. Neurosci Lett. 2014; 573:7-12

Non-Patent Document 4: Nittis T, Guittat L, LeDuc R D, Dao B, Duxin J P, Rohrs H, Townsend R R, Stewart S A.: Revealing novel telomere proteins using in vivo cross-linking, tandem affinity purification, and label-free quantitative LC-FTICR-MS. Mol Cell Proteomics. 2010; 9(6): 1144-56

SUMMARY OF THE INVENTION

Problems to be Solved by the Invention

The degree of purification of polypeptide is still low by subjecting a trace polypeptide existing in a biological sample such as plasma or serum abundantly containing impurity substances to single affinity purification. Accordingly, the impurity substances suppress the ionization of the polypeptide to be measured, and the function of the mass spectrometry cannot be sufficiently exerted, and thus measurement of the polypeptide becomes difficult (Non-patent Document 3). The smaller the amount of the polypeptide to be measured, the more difficult the measurement of the polypeptide becomes.

As a method for reducing non-specifically adsorbed substances, a method is reported which includes subjecting a protein to which two kinds of tags are fused in a genetic engineering manner to affinity purification twice consecutively (Non-patent Document 4). This method, however, is not applicable to a biological sample such as plasma or serum for which tagging cannot be made.

In light of the above, an object of the present invention is to provide a method for measuring a target trace polypeptide in a biological sample abundantly containing impurities by mass spectrometry. In particular, an object of the present invention is to provide a method for measuring a target trace polypeptide in a plasma or serum sample abundantly containing impurities by mass spectrometry.

Means for Solving the Problems

As a result of diligent efforts, the present inventor has attained the present invention by subjecting a trace polypeptide in a biological sample such as plasma or serum to affinity purification using an antibody having an epitope for a sequence in the polypeptide twice consecutively, and then conducting measurement by mass spectrometry. The affinity purification includes a variety of purification methods using an antibody, and includes not only immunoprecipitation but also other purification methods using an antibody (affinity chromatography including column, pipette chip, micro flow channel, spin column and the like).

The present invention includes the following aspects.

(1) A method for measuring a target polypeptide in a biological sample, the method comprising:

a first reaction step of bringing a liquid containing a biological sample into contact with a first antibody-immobilizing carrier that includes a carrier and an antibody bound to the carrier and having an antigen binding site capable of recognizing a target polypeptide, to bind the target polypeptide in the biological sample with the first antibody-immobilizing carrier;

a first washing step of washing the first antibody-immobilizing carrier to which the target polypeptide is bound;

a first eluting step of dissociating and eluting the target polypeptide from the first antibody-immobilizing carrier by using an acidic solution to obtain a first eluate;

a neutralizing step of making pH of the eluate neutral by adding a neutral buffer to the first eluate to obtain a first purified solution with neutralized pH;

a second reaction step of bringing the first purified solution into contact with a second antibody-immobilizing carrier that includes a carrier and an antibody bound to the carrier and having an antigen binding site capable of recognizing the target polypeptide, to bind the target polypeptide in the first purified solution with the second antibody-immobilizing carrier;

a second washing step of washing the second antibody-immobilizing carrier to which the target polypeptide is bound;

a second eluting step of dissociating and eluting the target polypeptide from the second antibody-immobilizing carrier by using an acidic solution to obtain a second purified solution; and a step of detecting the target polypeptide in the second purified solution by mass spectrometry.

In this specification, the "polypeptide" to be measured also includes a "peptide" and a "protein".

In the first antibody-immobilizing carrier and the second antibody-immobilizing carrier, the antibody should be an antibody having an antigen binding site capable of recognizing a target polypeptide. The antibody should be selected, for example, from the group consisting of an immunoglobulin having an antigen binding site capable of recognizing a target polypeptide and an immunoglobulin fragment containing an antigen binding site capable of recognizing a target polypeptide. The antibodies in the first antibody-immobilizing carrier and in the second antibody-immobilizing carrier may be the same or different from each other.

(2) The method according to (1), wherein a liquid amount of the first purified solution subjected to the second reaction step is smaller than a liquid amount of the liquid containing a biological sample subjected to the first reaction step.

(3) The method according to (1) or (2), wherein an amount of the second antibody-immobilizing carrier in the second reaction step is smaller than an amount of the first antibody-immobilizing carrier in the first reaction step.

(4) The method according to any one of (1) to (3), wherein in the first eluting step, the acidic solution is an acidic solution containing a surfactant.

(5) The method according to any one of (1) to (4), wherein in the second eluting step, the acidic solution is an acidic solution containing an organic solvent.

(6) The method according to any one of (1) to (5), wherein the biological sample is whole blood, plasma or serum.

(7) The method according to any one of (1) to (6), wherein the target polypeptide is a peptide.

(8) The method according to any one of (1) to (6), wherein the target polypeptide is an Aβ-related peptide.

(9) The method according to any one of (1) to (8), wherein in the mass spectrometry, a matrix-assisted laser desorption/ionization mass spectrometer is used.

Effects of the Invention

According to the present invention, by conducting affinity purification twice consecutively, the impurity substances that have not been excluded only with the first affinity purification can be further reduced with the second affinity purification. Therefore, it is possible to prevent suppression of ionization of polypeptides by the impurity substances, and it becomes possible to measure even a trace polypeptide in a biological sample by mass spectrometry. This method can be applied to a polypeptide in a biological sample to which a tag cannot be fused in a genetic engineering manner.

In the present invention, when the liquid amount of the first purified solution subjected to the second reaction step is smaller than the liquid amount of the liquid containing a biological sample (normally, containing a biological sample and a binding solution) subjected to the first reaction step, the binding efficiency of the antibody with the target polypeptide in the second reaction step is elevated, and loss of the target polypeptide can be further reduced. That is, in many cases, since the binding rate of the antibody with the target polypeptide in the affinity purification is not 100%, loss of the target polypeptide occurs more or less every time the affinity purification is conducted. The impurity substances are much reduced by conducting the affinity purification twice consecutively as compared with the case of conducting the affinity purification only once; however, the target polypeptide is simultaneously reduced as well. For this reason, in order to reduce loss of the target polypeptide by increasing the binding efficiency of the antibody with the target polypeptide in the second time, it is preferred to reduce the reaction solution amount (namely, the liquid amount of the first purified solution) in the second affinity purification.

In the present invention, when the amount of the second antibody-immobilizing carrier in the second reaction step is smaller than the amount of the first antibody-immobilizing carrier in the first reaction step, a liquid amount of the eluate which is to be a sample solution at the time of measurement by mass spectrometry (second purified solution) can be made small, with the result that the target polypeptide is further concentrated, and can be detected with high sensitivity. That is, detection with high sensitivity can be conducted by using a smaller amount of the sample solution at the time of measurement by mass spectrometry. For reducing the liquid amount of the eluate which is to be a sample solution at the time of measurement by mass spectrometry, it is preferred to reduce the amount of the antibody-immobilizing carrier used in the second affinity purification. It is also effective to reduce contamination with non-specifically adsorbed substances or impurity substances derived from antibody-immobilizing carriers.

MODES FOR CARRYING OUT THE INVENTION

Figure 1:
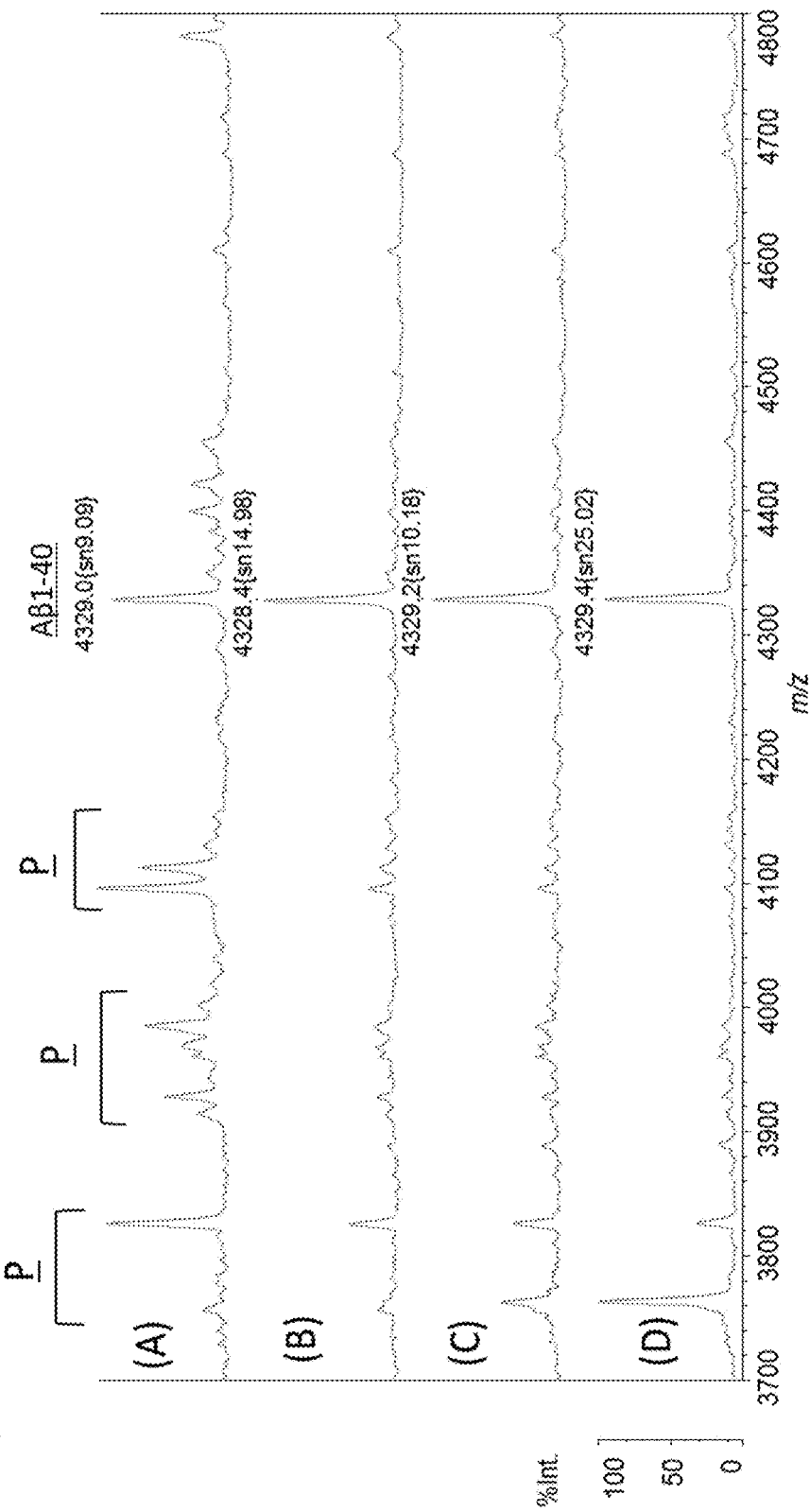
FIG. 1 shows the results of measurement by MALDI-MS after the conventional IP operation with the use of four different quantities of the anti-Aβ F(ab')-immobilizing beads targeting Aβ in a plasma sample in Experimental Example 5, in which (A) shows the result for the number of beads: approximately $10 \times 10^7$ beads, (B) shows the result for the number of beads: approximately $4 \times 10^7$ beads, (C) shows the result for the number of beads: approximately $2 \times 10^7$ beads, and (D) shows the result for the number of beads: approximately $1 \times 10^7$ beads, the horizontal axis indicates m/z, and the vertical axis indicates relative intensity of ion.

The method of the present invention is a method for measuring a target polypeptide in a biological sample, and comprises:

a first reaction step of bringing a liquid containing a biological sample into contact with a first antibody-immobilizing carrier that includes a carrier and an antibody bound to the carrier and having an antigen binding site capable of recognizing a target polypeptide, to bind the target polypeptide in the biological sample with the first antibody-immobilizing carrier;

a first washing step of washing the first antibody-immobilizing carrier to which the target polypeptide is bound;

a first eluting step of dissociating and eluting the target polypeptide from the first antibody-immobilizing carrier by using an acidic solution to obtain a first eluate;

a neutralizing step of making pH of the eluate neutral by adding a neutral buffer to the first eluate to obtain a first purified solution with neutralized pH;

a second reaction step of bringing the first purified solution into contact with a second antibody-immobilizing carrier that includes a carrier and an antibody bound to the carrier and having an antigen binding site capable of recognizing the target polypeptide, to bind the target polypeptide in the first purified solution with the second antibody-immobilizing carrier;

a second washing step of washing the second antibody-immobilizing carrier to which the target polypeptide is bound;

a second eluting step of dissociating and eluting the target polypeptide from the second antibody-immobilizing carrier by using an acidic solution to obtain a second purified solution; and a step of detecting the target polypeptide in the second purified solution by mass spectrometry.

The "polypeptide" to be measured includes a "peptide" and a "protein". A polypeptide, a peptide and a protein includes various entities. More specifically, they may be Aβ-related peptides. The "Aβ-related peptides" also include Aβ generated by cleavage of amyloid precursor proteins (APP) and peptides containing at least part of the sequence of Aβ. In Examples, the case of using Aβ-related peptides is illustrated.

[1. Antibody-Immobilizing Carrier]

The antibody-immobilizing carrier used in the present invention should be an antibody-immobilizing carrier consisting of a carrier, and an antibody bound to the carrier and having an antigen binding site capable of recognizing a target polypeptide. The antibody should be selected, for example, from the group consisting of an immunoglobulin having an antigen binding site capable of recognizing the target polypeptide and an immunoglobulin fragment containing an antigen binding site capable of recognizing the target polypeptide. The antibodies in the first antibody-immobilizing carrier and in the second antibody-immobilizing carrier may be the same or different from each other.

Examples of the immunoglobulin include IgG, IgM, IgA, IgY, IgD, and IgE. Examples of IgG include IgG1, IgG2, IgG3, and IgG4. Examples of the immunoglobulin having an antigen binding site capable of recognizing Aβ-related peptides (hereinafter, also referred to as "Aβ-related peptide antibody") include 6E10, 4G8, 1E11, 11A50-B10, 12F4, 9C4, 82E1, 12B2, 1A10, and the like. These antibodies are known as anti-amyloid beta antibodies. The immunoglobulin fragment containing an antigen binding site capable of recognizing Aβ-related peptides can be selected, for example, from the group consisting of F(ab')$_2$, F(ab'), F(ab), Fd, Fv, L chain, and H chain. The anti-Aβ-related peptide antibody to be immobilized to the carrier may be a monoclonal antibody or a polyclonal antibody. The antibody-immobilizing carrier used in the present invention can be an antibody-immobilizing carrier in which the above anti-Aβ-related peptide antibody and/or anti-Aβ-related peptide antibody fragment is immobilized to a carrier by an appropriate method.

The material of the carrier used herein may be a known material, and for example, may be selected from the group consisting of agarose, sepharose, dextran, silica gel, polyacrylamide, polystyrene, polyethylene, polypropylene, polyester, polyacrylonitrile, (meth)acrylic acid polymer, fluororesin, metal complex resin, glass, metal, and a magnetic substance.

The carrier may have any shape including a planar shape, a globular shape and other shapes. For example, the carrier may be a chip, or beads or may form a flow channel wall inside a micro device used for separation and/or concentration of a target substance. The carrier surface has a bonding functional group.

The antibody may be bound to the carrier via a spacer. As the spacer, those known in the art can be used, and an example thereof includes a high molecular weight polymer. Examples of the high molecular weight polymer include an alkylene group and an oxyalkylene group.

For example, the spacer may be an organic high molecular weight polymer selected from the group consisting of polyoxyalkylated polyol, polyvinyl alcohol, polyvinyl alkyl ether, polysaccharide, biodegradable polymer, and lipid polymer. The alkyl group in the polyoxyalkylated polyol and the polyvinyl alkyl ether may be, for example, a C1 to C6 alkyl group, preferably a C1 to C3 alkyl group. Examples of the polysaccharide include dextran, mucopolysaccharide, and chitins. An example of the mucopolysaccharide includes hyaluronic acid. Examples of the biodegradable polymer include PLA (poly(lactic acid)) and PLGA (poly(lactic-glycolic acid)).

The spacer in the present invention may be those containing one kind of the above examples, or may be those containing two or more kinds arbitrarily selected from the above examples. The spacer may be linear or branched.

The antibody-immobilizing carrier used in the present invention can be prepared by binding a carrier, and an antibody, and a spacer substance if used, via respective boding functional groups such as a covalently bonding functional group, an ionic-bonding functional group, and a hydrogen bonding functional group possessed by these elements by a known method depending on the kinds of the functional groups. In the present invention, the first antibody-immobilizing carrier and the second antibody-immobilizing carrier may be the same or different from each other.

[2. First Binding Reaction Step]

First, a liquid containing a biological sample (normally, containing a biological sample and a binding solution) is brought into contact with the first antibody-immobilizing carrier, to bind the first antibody-immobilizing carrier with a target polypeptide contained in the biological sample.

The biological sample includes body fluids such as blood, cerebrospinal fluid (CSF), urine, body secretory fluid, saliva, and sputum; and feces. The blood sample includes whole blood, plasma, serum and the like. The blood sample can be prepared by appropriately treating whole blood collected from an individual. The treatment conducted in the case of preparing a blood sample from collected whole blood is not particularly limited, and any treatment that is clinically acceptable may be conducted. For example, centrifugal separation or the like may be conducted. The blood sample subjected to the binding step may be appropriately stored at low temperature by freezing in the intermediate stage of the preparation step or in the post stage of the preparation step. In the present invention, the biological sample is disposed of rather than being returned to the individual from which the blood sample is derived. The use of a blood sample as a subject sample is preferable in that collection of a sample is minimally invasive when the sample is solid or cerebrospinal fluid, and that a blood sample is a subject sample for screening of various diseases in a general medical examination, a thorough physical examination and the like.

As the binding solution, a binding solution that is used in ordinary immunoprecipitation (IP) can be used. The composition of the binding solution preferably includes a surfactant for suppressing non-specific adsorption. As the surfactant, preferred is a neutral surfactant that is less likely to cause denaturation of protein such as antibody, is easily removed in the washing step, and does not suppress a signal of the target polypeptides even if the surfactant is contaminated in the subsequent mass spectrometry. Specific examples of the surfactant include a neutral surfactant having maltose in a hydrophilic part, a neutral surfactant having trehalose in a hydrophilic part, and a neutral surfactant having glucose in a hydrophilic part. The hydrophobic part of such a neutral surfactant is, but not particularly limited to, preferably an about C7 to C14 alkyl group. The binding solution is preferably a neutral buffer containing the surfactant selected from the above-mentioned surfactants.

Examples of the neutral surfactant having maltose in a hydrophilic part include:
n-Decyl-β-D-maltoside (DM) [cmc: 0.087%]
n-Dodecyl-β-D-maltoside (DDM) [cmc: 0.009%]
n-Nonyl-β-D-thiomaltoside (NTM) [cmc: 0.116%], and the like. The "cmc" represents critical micelle concentration.

Examples of the neutral surfactant having trehalose in a hydrophilic part include:
α-D-Glucopyranosyl-α-Dglucopyranoside monooctanoate (Trehalose C8) [cmc: 0.262%]
α-D-Glucopyranosyl-α-Dglucopyranoside monododecanoate (Trehalose C12) [cmc: 0.008%]
α-D-Glucopyranosyl-α-Dglucopyranoside monomyristate (Trehalose C14) [cmc: 0.0007%], and the like.

Examples of the neutral surfactant having glucose in a hydrophilic part include:
n-Octyl-β-D-thioglucoside (OTG) [cmc: 0.278%]
n-Octyl-β-D-glucoside (OG) [cmc: 0.731%]
n-Heptyl-β-D-thioglucoside (HTG) [cmc: 0.883%], and the like.

One or a combination of two or more of the aforementioned neutral surfactants can be used. The neutral surfactant to be used is selected appropriately depending on the carrier, the antibody and the target polypeptides to be used.

The neutral buffer as the binding solution has a surfactant concentration of, for example, 0.001 to 10% (v/v), preferably 0.01 to 5% (v/v), more preferably 0.05 to 2% (v/v), although the surfactant concentration is not particularly limited. By employing such a surfactant concentration, binding reaction between the antibody and the target polypeptides to be bound is likely to occur satisfactorily. The neutrality of the neutral buffer means about pH 6.5 to 8.5. Examples of the buffer composition include a Tris buffer, a phosphate buffer, a HEPES buffer, and the like.

Further, prior to the first binding step, a blood sample may be subjected to a pretreatment. In the pretreatment, for example, antibodies such as IgG and IgM contained in the blood sample are removed. The blood sample contains antibodies derived from the sample that bind with the antibody immobilized to the carrier for use in the binding step. Therefore, by removing the antibodies derived from the sample prior to the binding step, it is possible to prevent the antibodies derived from the sample from binding with the antibody used in the binding step. The antibodies derived from the sample can be removed by bringing the blood sample into contact with carriers to which Protein G, Protein A, Protein L, an anti-IgG antibody, an anti-IgM antibody, an anti-IgA antibody, an anti-IgY antibody, an anti-IgD antibody, an anti-IgE antibody and the like are bound. In the present invention, since the affinity purification is conducted twice consecutively, a pretreatment for a blood sample prior to the first binding step may not be conducted.

[3. First Washing Step]

Next, a bound body of the first antibody-immobilizing carrier and the target polypeptide obtained by the first binding step is washed with the use of a washing solution.

In the washing step, it is preferred first, washing is conducted by using a neutral buffer containing a surfactant as the washing solution, and then washing is conducted by using a neutral buffer not containing a surfactant as the washing solution.

As the neutral buffer containing a surfactant as the washing solution, those similar to the neutral buffer containing a surfactant as the binding solution described above can be used. First, by conducting washing with the use of the neutral buffer containing a surfactant, unnecessary components such as highly hydrophobic blood protein, lipid, and glycolipid are ordinarily removed. The neutrality of the neutral buffer is preferably pH closer to that of the body fluid, and for example, pH 6.5 to 8.5 is preferred, and pH 7.0 to 8.0 is more preferred. By washing with such a neutral buffer, it is possible to prevent the target polypeptides in the antigen antibody bound body from being dissociated from the carrier in this washing step.

Then, it is preferred to conduct washing with a neutral buffer not containing a surfactant. By washing with a neutral buffer not containing a surfactant, inconvenience such as bubbling in the subsequent operation is easily prevented.

In the washing step, by subjecting the carrier surface to a fluid pressure of 0.01 to 500 MPa, preferably 0.05 to 300 MPa, more preferably 0.1 to 200 MPa of the washing solution, unnecessary components can be removed. If the fluid pressure is below the aforementioned range, a desired washing effect tends not to be obtained. If the fluid pressure exceeds the aforementioned range, the binding between the antibody and the bound target polypeptide may be cleaved. By conducting the washing in a higher pressure condition, it is possible to improve the efficiency of removing non-specific adsorbed substance on the antibody-immobilizing carrier, and this contributes to improvement in sensitivity of analysis (improvement in S/N ratio) of the bound target polypeptide.

A specific technique for washing is not particularly limited. For example, in the case of a globular carrier, it can be washed by stirring in a washing liquid. In the case of a planar carrier, it can be washed by spraying a high-pressure washing liquid from a washing nozzle. More specifically, in order to wash a specific region on the planar carrier under high pressure, a washing nozzle having an inner diameter suited for the area of the region can be used. This nozzle is formed of, for example, a double tube in which the inner tube can be functioned exclusively for water injection for spraying the washing liquid onto the carrier surface, and the outer tube can be functioned exclusively for water ejection for sucking the washing liquid sprayed on the carrier surface.

[4. First Dissociating and Eluting Step]

Next, for the bound body of the first antibody-immobilizing carrier and the target polypeptide after washing, the target polypeptide is dissociated from the antibody-immobilizing carrier by using an acidic aqueous solution as an eluent.

In order to dissociate an antigen from an antibody to which the antigen is bound (antigen-antibody complex), an acidic aqueous solution is brought into contact with the antigen-antibody complex. In the present invention, the target polypeptide is dissociated and eluted from the antibody-immobilizing carrier to which the target polypeptide is bound by using an acidic aqueous solution.

The acidic aqueous solution preferably contains a surfactant. When a surfactant is contained in the acidic aqueous solution, dissociation of the target polypeptide from the carrier occurs efficiently. As a result, this contributes to improvement in recovery of the bound target polypeptide. If the concentration of the surfactant is less than the CMC, the effect of the surfactant is not obtained, and the efficiency of dissociation of the target polypeptide is not excellent. For example, by using an aqueous solution containing 0.1% DDM in 50 mM Glycine buffer (pH 2.8), a higher elution efficiency is easily obtained. The acidity of the acidic aqueous solution means about pH 1 to 3.5.

Also, when the surfactant is contained in the acidic aqueous solution, it is effective for preventing the eluted target polypeptide from being adsorbed to a tube, a test tube, a microplate or the like, and for suppressing loss of the target polypeptide due to such adsorption.

Normally, the acidic aqueous solution containing the surfactant used for dissociation can be used also as an eluent to elute the target polypeptide dissociated from the carrier. Alternatively, a person skilled in the art can select the eluent appropriately. In the first dissociating and eluting step, the acidic aqueous solution does not preferably contain an organic solvent so as not to deteriorate the reaction efficiency in the next second reaction step.

In the dissociating step, by bringing the carrier surface into contact with the eluent, the target polypeptide can be dissociated and eluted. The carrier may be stirred in the eluent as is necessary. In this manner, a first eluate is obtained.

[5. Neutralizing Step]

The pH of the eluate is neutralized by adding a neutral buffer to the obtained first eluate, and thus a first purified solution with neutralized pH is obtained. In the neutralizing step, as the neutral buffer, those similar to the neutral buffer as the binding solution described above can be used. The neutral buffer preferably contains a surfactant. The neutrality of the neutral buffer is preferably pH closer to that of the body fluid, and for example, pH 6.5 to 8.5 is preferred, and pH 7.0 to 8.0 is more preferred. As the pH of the first purified solution, for example, pH 6.5 to 8.5 is preferred, and pH 7.0 to 8.0 is more preferred. By employing such a pH range, high reaction efficiency in the next second reaction step is easily obtained. Further, in the neutralizing step, the neutral buffer preferably does not contain an organic solvent so as not to deteriorate the reaction efficiency in the next second reaction step.

[6. Second Binding Reaction Step]

Next, the first purified solution is brought into contact with the second antibody-immobilizing carrier, to bind the second antibody-immobilizing carrier with the target polypeptide contained in the first purified solution.

The first purified solution has already contained a binding solution by the aforementioned operation. However, a binding solution that is the same as that in the first binding reaction step, and is used in the ordinary immunoprecipitation method (IP) may further be added in this stage.

Preferably, the liquid amount of the first purified solution subjected to the second reaction step is smaller than the liquid amount of the liquid containing a biological sample (biological sample liquid containing the biological sample and a binding solution) subjected to the first reaction step. In the present invention, when the liquid amount of the first purified solution subjected to the second reaction step is smaller than the liquid amount of the biological sample liquid subjected to the first reaction step (that is, the total liquid amount of the biological sample and the binding solution), the binding efficiency of the antibody with the target polypeptide in the second reaction step is elevated, and loss of the target polypeptide can be further reduced. That is, in many cases, since the binding rate of the antibody with the target polypeptide in the affinity purification is not 100%, loss of the target polypeptide occurs more or less every time the affinity purification is conducted. The impurity substances are much reduced by conducting the affinity purification twice consecutively as compared with the case of conducting the affinity purification only once; however, the target polypeptide is simultaneously reduced as well. For this reason, in order to reduce loss of the target polypeptide by increasing the binding efficiency of the antibody with the target polypeptide in the second time, it is preferred to reduce the reaction solution amount (namely, the liquid amount of the first purified solution) in the second affinity purification.

Preferably, the liquid amount of the first purified solution subjected to the second reaction step is made smaller as compared with the liquid amount of the biological sample liquid subjected to the first reaction step (namely, the total liquid amount of the biological sample and the binding solution). The liquid amount of the first purified solution subjected to the second reaction step may be, for example, about 0.1 to 50%, preferably about 0.5 to 20%, more preferably about 1 to 10% by volume, on the basis of the liquid amount of the biological sample liquid subjected to the first reaction step. This can be achieved in such a manner that the liquid amount of the first purified solution is reduced by reducing the amount of the first eluate with reduction of the amount of the acidic solution used in the first eluting step, by reducing the amount of the neutral buffer used in the neutralizing step, or the like.

Preferably, the amount of the second antibody-immobilizing carrier in the second reaction step is smaller than the amount of the first antibody-immobilizing carrier in the first reaction step. In the present invention, when the amount of the second antibody-immobilizing carrier in the second reaction step is smaller than the amount of the first antibody-immobilizing carrier in the first reaction step, a liquid amount of the eluate which is to be a sample solution at the time of measurement by mass spectrometry (second purified solution) can be made small, with the result that the target polypeptide is further concentrated, and can be detected with high sensitivity. That is, the target polypeptide is further concentrated and detection with highly sensitivity can be conducted by using a smaller amount of the sample solution at the time of measurement by mass spectrometry. For reducing the liquid amount of the eluate which is to be a sample solution at the time of measurement by mass spectrometry, it is preferred to reduce the amount of the antibody-immobilizing carrier used in the second affinity purification. It is also effective to reduce contamination with non-specifically adsorbed substances or impurity substances derived from antibody-immobilizing carriers.

The amount of the second antibody-immobilizing carrier in the second reaction step may be, for example, about 1 to 50%, preferably about 5 to 25% by surface area of the carrier, on the basis of the amount of the first antibody-immobilizing carrier in the first reaction step. When the first antibody-immobilizing carrier and the second antibody-immobilizing carrier are the same carrier, the surface area of the carrier is synonymous to the weight of the carrier, and the number of carriers.

[7. Second Washing Step]

A bound body of the second antibody-immobilizing carrier and the target polypeptide obtained in the second binding step is washed with the use of a washing solution.

In the washing step, it is preferred first, washing is conducted by using a neutral buffer containing a surfactant as the washing solution, and then washing is conducted by using a neutral buffer not containing a surfactant as the washing solution.

As the neutral buffer containing a surfactant as the washing solution, those similar to the neutral buffer containing a surfactant as the binding solution described above can be used. First, by conducting washing with the use of the neutral buffer containing a surfactant, unnecessary components such as highly hydrophobic blood protein, lipid, and glycolipid are ordinarily removed. The neutrality of the neutral buffer is preferably pH closer to that of the body fluid, and for example, pH 6.5 to 8.5 is preferred, and pH 7.0 to 8.0 is more preferred. By washing with such a neutral buffer, it is possible to prevent the target polypeptide in the antigen antibody bound body from being dissociated from the carrier in this washing step.

Then, it is preferred to conduct washing with a neutral buffer not containing a surfactant. By washing with a neutral buffer not containing a surfactant, inconvenience such as bubbling in the subsequent operation is easily prevented. Further, it is possible to reduce ionization suppression (ion suppression) due to contamination with a surfactant in the detecting step.

In the washing step, by subjecting the carrier surface to a fluid pressure of 0.01 to 500 MPa, preferably 0.05 to 300 MPa, more preferably 0.1 to 200 MPa of the washing solution, unnecessary components can be removed. If the fluid pressure is below the aforementioned range, a desired washing effect tends not to be obtained. If the fluid pressure exceeds the aforementioned range, the binding between the antibody and the bound target polypeptide may be cleaved. By conducting the washing in a higher pressure condition, it is possible to improve the efficiency of removing non-specific adsorbed substance on the antibody-immobilizing carrier, and this contributes to improvement in sensitivity of analysis (improvement in S/N ratio) of the bound target polypeptide.

A specific technique for washing is similar to that described in the first washing step, and is not particularly limited.

[8. Second Dissociating and Eluting Step]

Next, for the bound body of the second antibody-immobilizing carrier and the target polypeptide after washing, the target polypeptide is dissociated from the antibody-immobilizing carrier by using an acidic aqueous solution as an eluent.

In order to dissociate an antigen from an antibody to which the antigen is bound (antigen-antibody complex), an acidic aqueous solution is brought into contact with the antigen-antibody complex. In the present invention, the target polypeptide is dissociated and eluted from the antibody-immobilizing carrier to which the target polypeptide is bound by using an acidic aqueous solution. The acidic aqueous solution preferably contains an organic solvent. When an organic solvent is contained in the acidic aqueous solution, dissociation of the target polypeptide from the carrier occurs efficiently. As a result, this contributes to improvement in recovery of the bound target polypeptide. Examples of the organic solvent used in this case include organic solvents that mingle with water at an arbitrary ratio, such as acetonitrile, acetone, methanol, ethanol, isopropanol, chloroform and the like. While the concentration of the organic solvent in the acidic aqueous solution is not particularly limited, it is for example about 10 to 90% (v/v), preferably 20 to 80% (v/v), and more preferably about 25 to 70% (v/v). When the concentration of the organic solvent in the acidic aqueous solution falls within the aforementioned range, dissociation of the target polypeptide from the carrier occurs efficiently. This contributes to improvement in sensitivity of analysis (improvement in S/N ratio) of the bound target polypeptide. If the concentration of the organic solvent is less than 10% (v/v), the effect of the organic solvent is not obtained, and the efficiency of dissociation of the target polypeptide is not excellent. For example, by using an aqueous solution containing 70% (v/v) acetonitrile in 5 mM acetic acid, a higher elution efficiency is easily obtained. The acidity of the acidic aqueous solution means about pH 1 to 3.5.

Normally, the acidic aqueous solution containing the organic solvent used for dissociation can be used also as an eluent to elute the target polypeptide dissociated from the carrier. Alternatively, a person skilled in the art can select the eluent appropriately.

In the dissociating step, by bringing the carrier surface into contact with the eluent, the target polypeptide can be dissociated and eluted. The carrier may be stirred in the eluent as is necessary. In this manner, a second purified solution is obtained.

[9. Detecting Step]

Next, the target polypeptide contained in the obtained second purified solution is detected by mass spectrometry. The mass spectrometry is preferably mass spectrometry such as matrix-assisted laser desorption/ionization (MALDI) mass spectrometry or electrospray ionization (ESI) mass spectrometry. For example, a MALDI-TOF (matrix-assisted laser desorption/ionization—time of flight) mass spectrometer, a MALDI-IT (matrix-assisted laser desorption/ionization—ion trap) mass spectrometer, a MALDI-IT-TOF (matrix-assisted laser desorption/ionization—ion trap—time of flight) mass spectrometer, a MALDI-FTICR (matrix-assisted laser desorption/ionization—Fourier transformation ion cyclotron resonance) mass spectrometer, an ESI-QqQ (electrospray ionization—triple quadrupole) mass spectrometer, an ESI-Qq-TOF (electrospray ionization—tandem quadrupole—time of flight) mass spectrometer, an ESI-FTICR (electrospray ionization—Fourier transformation ion cyclotron resonance) mass spectrometer or the like can be employed.

A matrix and a matrix solvent can be appropriately determined by a person skilled in the art depending on the analysis subject (polypeptide).

As the matrix, for example, α-cyano-4-hydroxycinnamic acid (CHCA), 2,5-dihydroxybenzoic acid (2,5-DHB), sinapic acid, 3-aminoquinoline (3-AQ) or the like can be used.

The matrix solvent can be selected from the group consisting of, for example, acetonitrile (ACN), trifluoroacetic acid (TFA), methanol, ethanol and water, and used. More specifically, an ACN-TFA aqueous solution, an ACN aqueous solution, methanol-TFA aqueous solution, a methanol aqueous solution, an ethanol-TFA aqueous solution, an ethanol solution or the like can be used. The concentration of ACN in the ACN-TFA aqueous solution can be, for example, 10 to 90% by volume, the concentration of TFA can be, for example, 0.05 to 1% by volume, preferably 0.05 to 0.1% by volume.

The matrix concentration can be, for example, 0.1 to 50 mg/mL, preferably 0.1 to 20 mg/mL, or 0.3 to 20 mg/mL, further preferably 0.5 to 10 mg/mL.

In the case of employing MALDI mass spectrometry as a detecting system, a matrix additive (comatrix) is preferably used together. The matrix additive can be appropriately selected by a person skilled in the art depending on the analysis subject (polypeptides) and/or the matrix. For example, as the matrix additive, a phosphonic acid group-containing compound can be used. Specific examples of a compound containing one phosphonic acid group include phosphonic acid, methylphosphonic acid, phenylphosphonic acid, 1-naphthylmethylphosphonic acid, and the like. Examples of a compound containing two or more phosphonic acid groups include methylenediphosphonic acid (MDPNA), ethylenediphosphonic acid, ethane-1-hydroxy-1,1-diphosphonic acid, nitrilotriphosphonic acid, ethylenediaminetetraphosphonic acid, and the like. Among the aforementioned phosphonic acid group-containing compounds, compounds having two or more, preferably two to four phosphonic acid groups in one molecule are preferred.

The use of the phosphonic acid group-containing compound is useful, for example, when metal ions of the washing solution remaining on the surface of the antibody-immobilizing carrier are contaminated into the eluate after the dissociating step. The metal ions adversely affect on the background in the mass spectrometry. The use of the phosphonic acid group-containing compound is effective for suppressing such an adverse affect.

Besides the aforementioned matrix additive, a more common additive, for example, a substance that is selected from the group consisting of ammonium salts and organic bases may be used.

The matrix additive can be prepared as a solution of 0.1 to 10 w/v %, preferably 0.2 to 4 w/v % in water or in a matrix solvent. The matrix additive solution and the matrix solution can be mixed in a volume ratio of, for example, 1:100 to 100:1, preferably 1:10 to 10:1.

EXAMPLES

Hereinafter, the present invention will be described specifically with reference to examples, but is not limited to these examples. In the following, the amount of a matter Experimental Example 1: Production of Anti-Aβ Antibody-Immobilizing Beads and Anti-Aβ F(Ab')-Immobilizing Beads A clone 6E10 (Covance) of an anti-Aβ antibody (IgG) recognizing the residues 3-8 of amyloid β protein (Aβ) as an epitope was prepared. Also a F(ab') fragment thereof was prepared as necessary.

For 100 µg of IgG or 26.4 µg of F(ab'), approximately $3.3 \times 10^8$ magnetic beads (Dynabeads (registered trade name) M-270 Epoxy) were caused to react in an immobilizing buffer (0.1 M phosphate buffer (pH 7.4) containing 1 M ammonium sulfate) at 37° C. for 16 to 24 hours to produce anti-Aβ IgG-immobilizing beads or anti-Aβ F(ab')-immobilizing beads.

Experimental Example 2: Operation Procedure of Conventional Immunoprecipitation Method (IP)

After mixing 250 µL of human plasma (Kohjin Bio) with an equivalent amount (250 µL) of a first IP reaction buffer (0.2% (w/v) DDM, 0.2% (w/v) NTM, 800 mM GlcNAc, 100 mM Tris-HCl, 300 mM NaCl, pH 7.4), the mixture was left still on ice for 5 minutes. The plasma was mixed with the anti-Aβ antibody-immobilizing beads, and shaken on ice for 1 hour. Then, the anti-Aβ antibody-immobilizing beads were washed five times with 100 µL of a washing buffer (0.1% DDM, 0.1% NTM, 50 mM Tris-HCl(pH 7.4), 150 mM NaCl), twice with 50 µL of a 50 mM ammonium acetate buffer, and once with 30 µL of $H_2O$, and then the substance bound to the anti-Aβ antibody-immobilizing beads was eluted with 5 µL of an eluent (70% (v/v) acetonitrile containing 5 mM hydrochloric acid). The resultant eluate was subjected to mass spectrometry.

Experimental Example 3: Operation Procedure of Consecutive Immunoprecipitation (cIP)

(First Reaction Step)
After mixing 250 µL of human plasma (Kohjin Bio) with an equivalent amount (250 µL) of a first IP reaction buffer (0.2% (w/v) DDM, 0.2% (w/v) NTM, 800 mM GlcNAc, 100 mM Tris-HCl, 300 mM NaCl, pH 7.4), the mixture was left still on ice for 5 minutes. The plasma was mixed with the anti-Aβ antibody-immobilizing beads, and shaken on ice for 1 hour.

(First Washing Step, First Eluting Step)
Then, the anti-Aβ antibody-immobilizing beads were washed three times with 100 µL of a first IP washing buffer (0.1% DDM, 0.1% NTM, 50 mM Tris-HCl (pH 7.4), 150 mM NaCl), and twice with 50 µL of a 50 mM ammonium acetate buffer, and then the substance bound to the anti-Aβ antibody-immobilizing beads was eluted with a first IP eluent (50 mM Glycine buffer containing 0.1% DDM (pH 2.8)). Thus, a first eluate was obtained.

(Neutralizing Step)
The obtained first eluate was mixed with a second IP reaction buffer (0.2% (w/v) DDM, 800 mM GlcNAc, 300 mM Tris-HCl, 300 mM NaCl, pH 7.4) to obtain a first purified solution.

(Second Reaction Step)
The obtained first purified solution was mixed with the anti-Aβ antibody-immobilizing beads and shaken on ice for 1 hour.

(Second Washing Step, Second Eluting Step)
Then, the anti-Aβ antibody-immobilizing beads were washed five times with 50 µL of a second washing buffer (0.1% DDM, 50 mM Tris-HCl(pH 7.4), 150 mM NaCl), twice with 50 µL of a 50 mM ammonium acetate buffer, and once with 30 µL of $H_2O$, and then the substance bound to the anti-Aβ antibody-immobilizing beads was eluted with 5 µL of a second IP eluent (70% (v/v) acetonitrile containing 5 mM hydrochloric acid). In this manner, a second purified solution was obtained. The second purified solution was subjected to mass spectrometry.

Experimental Example 4: Detection of Peptide by MALDI-TOF MS

As a matrix for Linear TOF, α-cyano-4-hydroxycinnamic acid (CHCA) was used. A matrix solution was prepared by dissolving 1 mg of CHCA in 1 mL of 70% (v/v) acetonitrile. As a matrix additive, 0.4% (w/v) methanediphosphonic acid (MDPNA) was used. After mixing equivalent amounts of a 1 mg/mL CHCA solution and 0.4% (w/v) MDPNA, 0.5 µL of the mixture was added dropwise on a Focus MALDI Plate™ 900 µm (Hudson Surface Technology, Inc., Fort Lee, N.J.) and dried to solid.

Each 1 µL of the eluate obtained by immunoprecipitation according to the procedure of Experimental Example 2 or Experimental Example 3 was taken and dropped to the matrix on a µFocus MALDI Plate™ 900 µm.

The mass spectrum data was acquired by Linear TOF in a positive ion mode by using AXIMA Performance (Shimadzu/KRATOS, Manchester, UK). Each of 16,000 shots was integrated per one well with 400 spots. The standard of the detection limit of the peak was an S/N ratio of not less than 3. A m/z value of Linear TOF was indicated by an average mass of peaks. The m/z value was calibrated by using human angiotensin II, human ACTH fragment 18-39, bovine insulin oxidized beta-chain, and bovine insulin as external standards.

[Evaluation]
Examples of various evaluations made in Experimental Examples 5 to 10 below are shown.

Experimental Example 5: Problem Associated with Conventional Immunoprecipitation Method In antibody antigen reaction, as the amount of antibody increases, the amount of antigen to be bound also increases. Therefore, when a sufficient amount of the target substance cannot be recovered by the immunoprecipitation, this problem may be solved by increasing the number of antibody-immobilizing beads. However, for a sample containing impurities, impurity substances that are non-specifically adsorbed to the antibody-immobilizing beads also increase as the number of the antibody-immobilizing beads increases. In particular, in plasma which is a biological sample abundantly containing impurity substances, impurity substances that are non-specifically adsorbed exist abundantly, so that ionization suppression (ion suppression) of the target substance is caused and the sensitivity is deteriorated in MALDI-MS.

According to the operation procedure of the conventional immunoprecipitation method (IP) in Experimental Example 2, eluates were obtained with the use of four different quantities of the anti-Aβ F(ab')-immobilizing beads (approximately $1\times10^7$ beads, $2\times10^7$ beads, $4\times10^7$ beads, $10\times10^7$ beads) targeting Aβ in a plasma sample, and the resultant eluates were measured by MALDI-MS. These results are shown in FIG. 1.

That is, FIG. 1 shows the results of measurement by MALDI-MS after the conventional IP operation with the use of four different quantities of the anti-Aβ F(ab')-immobilizing beads targeting Aβ in a plasma sample in Experimental Example 5, in which (A) shows the result for the number of beads: approximately $10\times10^7$ beads, (B) shows the result for the number of beads: approximately $4\times10^7$ beads, (C) shows the result for the number of beads: approximately $2\times10^7$ beads, and (D) shows the result for the number of beads: approximately $1\times10^7$ beads.

FIG. 1 reveals that as the number of beads increases, S/N of the Aβ1-40 peak decreases in height and peaks of the impurity substances derived from plasma increase in height. "P" in FIG. 1 indicates peaks of impurity substances derived from plasma.

Experimental Example 6: Comparison 1 Between Conventional Immunoprecipitation Method and Two Consecutive Immunoprecipitation Method of Present Invention For trace substances such as Aβ in plasma, detection with high sensitivity by MALDI-MS is difficult to be made because impurity substances cannot be excluded sufficiently by the conventional IP. In light of this, the present inventors attempted to effectively exclude impurities by conducting the two consecutive immunoprecipitation (cIP) to improve the sensitivity for Aβ.

For 250 μL of human plasma purchased from Kohjin Bio, an eluate was obtained according to the operation procedure of the conventional immunoprecipitation method (IP) in Experimental Example 2, and the eluate was measured by MALDI-MS. Meanwhile, for 250 μL of human plasma purchased from Kohjin Bio, a second purified solution was obtained according to the operation procedure of the consecutive immunoprecipitation method (cIP) in Experimental Example 3, and the second purified solution was measured by MALDI-MS. Regarding the anti-Aβ antibody-immobilizing beads, evaluation was made for each of the two kinds: anti-Aβ F(ab')-immobilizing beads and anti-Aβ IgG-immobilizing beads. These results are shown in FIG. 2 and FIG. 3.

Figure 2:
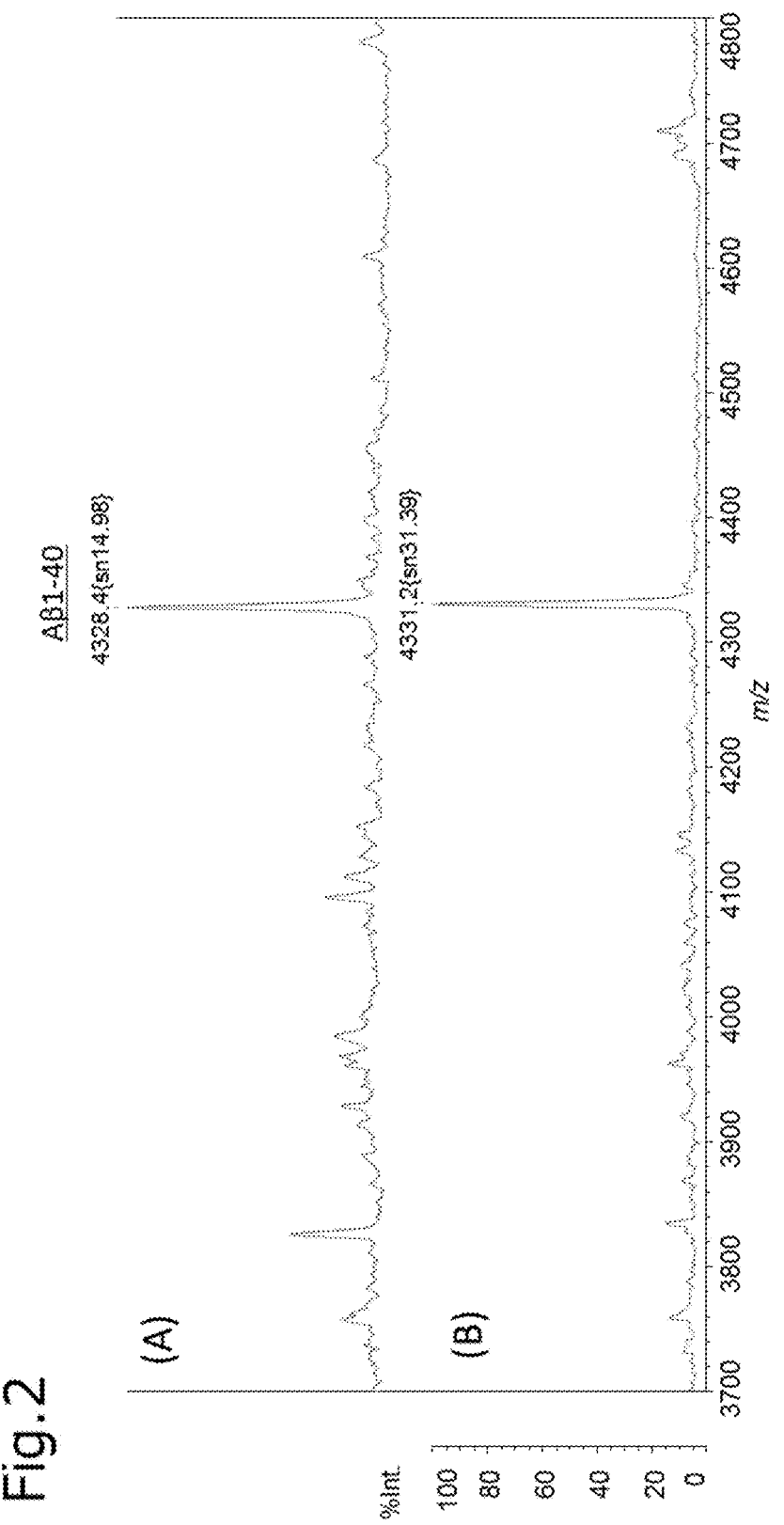
FIG. 2 shows the results of measurement by MALDI-MS after the immunoprecipitation operation with the use of the anti-Aβ F(ab')-immobilizing beads targeting Aβ in a plasma sample in Experimental Example 6, in which (A) shows the result of measurement by MALDI-MS after the conventional IP operation, and (B) shows the result of measurement by MALDI-MS after the cIP operation of the present invention.

That is, FIG. 2 shows the results of measurement by MALDI-MS after the immunoprecipitation operation with the use of the anti-Aβ F(ab')-immobilizing beads targeting Aβ in a plasma sample in Experimental Example 6, in which (A) shows the result of measurement by MALDI-MS after the conventional IP operation (anti-Aβ F(ab')-immobilizing beads: approximately $4\times10^7$ beads), and (B) shows the result of measurement by MALDI-MS after the cIP operation of the present invention (first anti-Aβ F(ab')-immobilizing beads: approximately $4\times10^7$ beads, second anti-A F(ab')-immobilizing beads: approximately $1\times10^7$ beads, first IP eluent amount: 30 μL, first purified solution: 100 μL).

Figure 3:
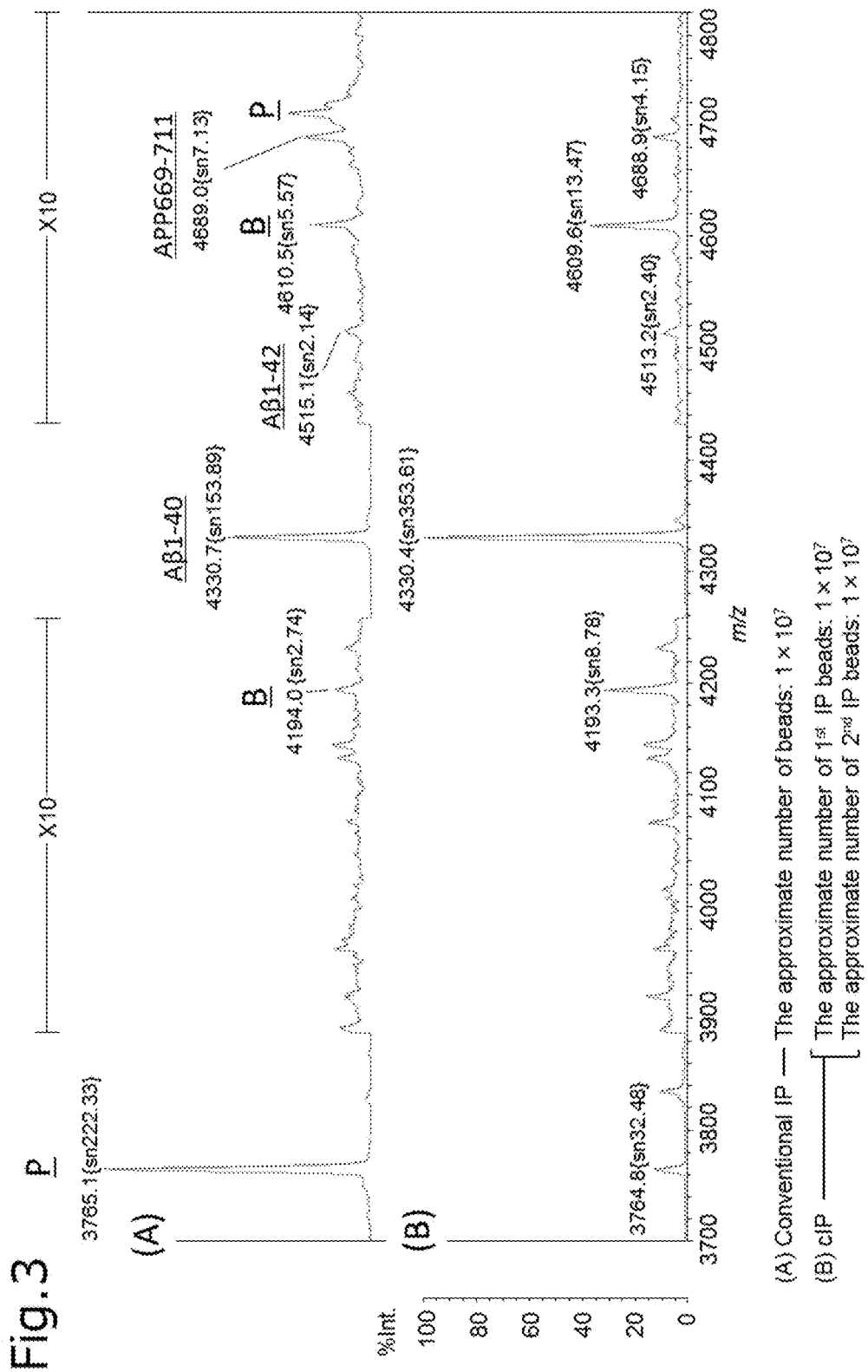
FIG. 3 shows the results of measurement by MALDI-MS after the immunoprecipitation operation with the use of the anti-Aβ IgG-immobilizing beads targeting Aβ in a plasma sample in Experimental Example 6, in which (A) shows the result of measurement by MALDI-MS after the conventional IP operation, and (B) shows the result of measurement by MALDI-MS after the cIP operation of the present invention.

FIG. 3 shows the results of measurement by MALDI-MS after the immunoprecipitation operation with the use of the anti-Aβ IgG-immobilizing beads targeting Aβ in a plasma sample in Experimental Example 6, in which (A) shows the result of measurement by MALDI-MS after the conventional IP operation (anti-Aβ IgG-immobilizing beads: approximately $1\times10^7$ beads), and (B) shows the result of measurement by MALDI-MS after the cIP operation of the present invention (first anti-Aβ IgG-immobilizing beads: approximately $1\times10^7$ beads, second anti-Aβ IgG-immobilizing beads: approximately $1\times10^7$ beads, first IP eluent amount: 15 μL, first purified solution: 30 μL). In FIG. 3, "P" indicates peaks of impurity substances derived from plasma, and "B" indicates peaks of impurity substances derived from antibody beads.

As shown in FIG. 2 and FIG. 3, S/N of Aβ1-40 peak was improved by the cIP than by the conventional IP for both cases using the anti-Aβ F(ab')-immobilizing beads and the anti-Aβ IgG-immobilizing beads. Regarding the anti-Aβ IgG-immobilizing beads, peaks of impurity substances derived from plasma were reduced by the cIP (FIG. 3).

Experimental Example 7: Comparison 2 Between Conventional Immunoprecipitation Method and Two Consecutive Immunoprecipitation Method of Present Invention In order to examine whether impurity substances can be excluded effectively by the cIP, the eluate sample after the operation of the conventional IP, and the second purified solution sample after the operation of the cIP of the present invention in the case of using the anti-Aβ IgG-immobilizing beads in Experimental Example 6 were applied to SDS-PAGE, respectively, and proteins were compared by silver staining.

Treatments 1 to 4 were conducted in the following manner.
1: Using Dynabeads M-270 Epoxy to which an antibody is not immobilized, the conventional IP operation was conducted once for plasma.
2: Anti-Aβ IgG-immobilizing beads were exposed to an eluent (70% (v/v) acetonitrile containing 5 mM hydrochloric acid).
3: Using the anti-Aβ IgG-immobilizing beads, IP was conducted once for plasma.
4: Using the anti-Aβ IgG-immobilizing beads, two consecutive IP (cIP) was conducted for plasma.

Figure 4:
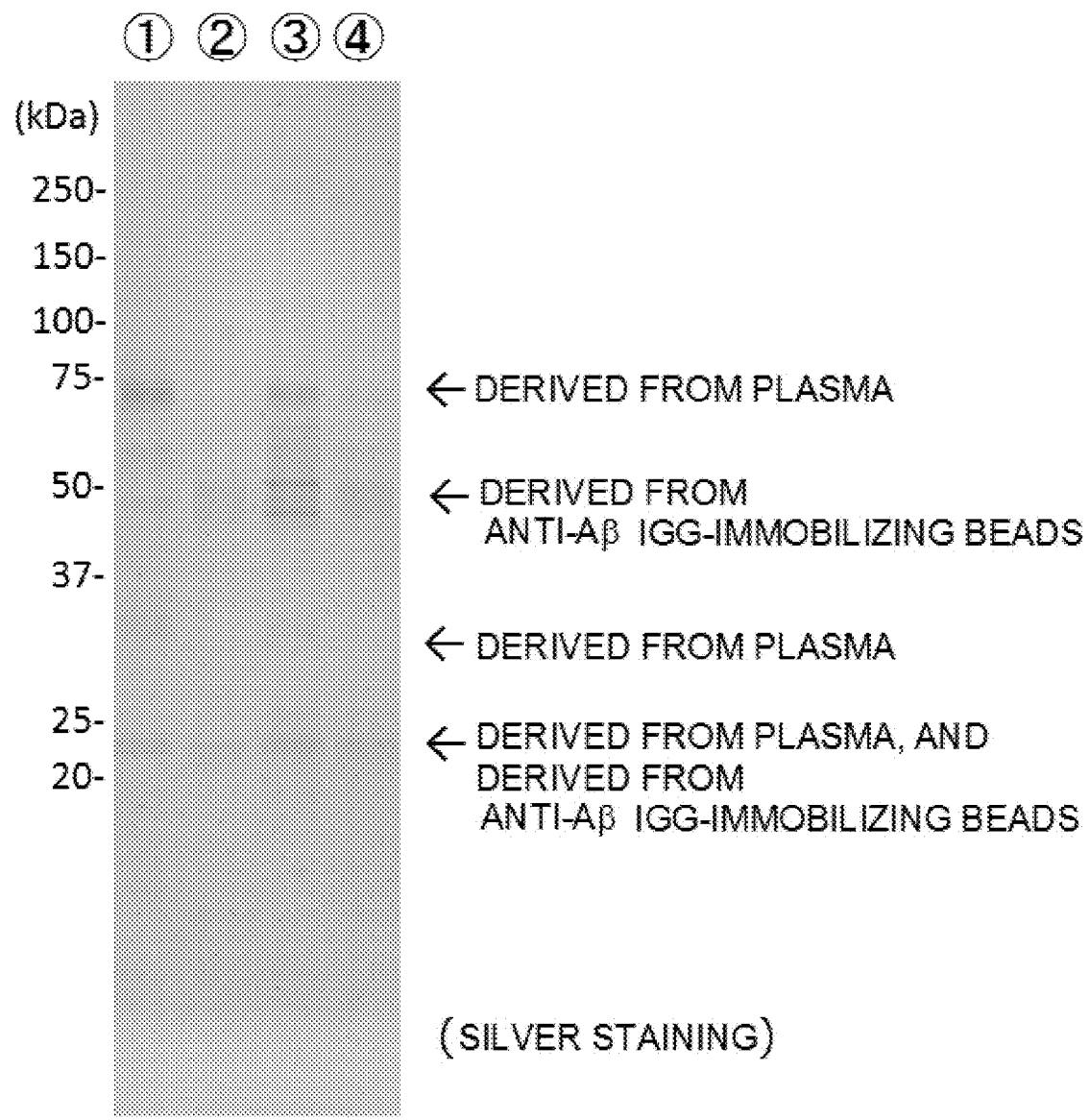
FIG. 4 shows the result of comparison between the eluate sample after the conventional IP operation and the second purified solution sample after the cIP operation of the present invention in the case of using the anti-Aβ IgG-immobilizing beads in Experimental Example 6, by applying them to SDS-PAGE and comparing protein by silver staining.

After conducting the treatments 1 to 4, the samples were applied to SDS-PAGE, and protein bands were detected by silver staining. The results are shown in FIG. 4. That is, FIG. 4 shows the result of comparison between the eluate sample after the conventional IP operation and the second purified solution sample after the cIP operation of the present invention in the case of using the anti-Aβ IgG-immobilizing beads in Experimental Example 6, by applying them to SDS-PAGE and comparing protein by silver staining.

TABLE 1

| Lane | Beads | Treatment | Note |
| --- | --- | --- | --- |
| 1 | Dynabeads M-270 Epoxy (no antibody) | Single IP | Protein derived from plasma non-specifically adsorbed to beads themselves |
| 2 | Anti-Aβ IgG-immobilizing beads | Without IP | Protein derived from anti-Aβ IgG-immobilizing beads |
| 3 | Anti-Aβ IgG-immobilizing beads | Single IP | Protein contained in first IP |
| 4 | Anti-Aβ IgG-immobilizing beads | Two consecutive IP | Protein contained in second IP |

The results of FIG. 4 indicated that protein is reduced in the cIP (lane: 4) than in the conventional single IP (lane: 3).

The protein band observed in the sample obtained by conducting the IP operation using Dynabeads M-270 Epoxy to which an antibody is not covalently bonded for plasma (lane: 1) was observed also in the sample after single IP (lane: 3), revealing that protein derived from plasma that is non-specifically absorbed was adsorbed to the beads themselves. When the anti-Aβ IgG-immobilizing beads were exposed to an eluent (70% (v/v) acetonitrile containing 5 mM hydrochloric acid), protein was eluted slightly (lane: 2). This protein band was observed also in the sample after the cIP (lane: 4), revealing that the protein detected by the cIP is a protein derived from the anti-Aβ IgG-immobilizing beads. In the sample after cIP, protein derived from plasma was excluded as much as possible, while contamination with protein derived from the anti-Aβ IgG-immobilizing beads was observed.

Experimental Example 8: Reaction Condition of cIP Effective for High-Sensitive Measurement of MALDI-MS: Second IP Reaction Solution Amount In antibody antigen reaction, the binding efficiency increases as the concentrations of antigen and antibody are high. Although the original sample concentration cannot be controlled in the first IP reaction of cIP, it is possible to increase the concentration of the substance to be subjected to the second IP reaction by reducing the amount of the eluate in the first IP reaction (first purified solution), so that the binding efficiency can be increased.

Thus, in a liquid containing a biological sample to be subjected to the first reaction step (plasma: 250 μL+reaction buffer: 250 μL) according to the consecutive immunoprecipitation cIP in Experimental Example 3, by using the anti-Aβ IgG-immobilizing beads (number of the anti-Aβ IgG-immobilizing beads in the first IP: approximately $4 \times 10^7$ beads, number of the anti-Aβ IgG-immobilizing beads in the second IP: approximately $1 \times 10^7$ beads), sensitivity in MALDI-MS was compared between the following cases (A) and (B):
(A) the first IP eluent amount was 45 μL, and the second IP reaction solution amount (liquid amount of the first purified solution) was 100 μL, and
(B) the first IP eluent amount was 15 μL, and the second IP reaction solution amount (liquid amount of the first purified solution) was 30 μL. These results are shown in FIG. 5.

Figure 5:
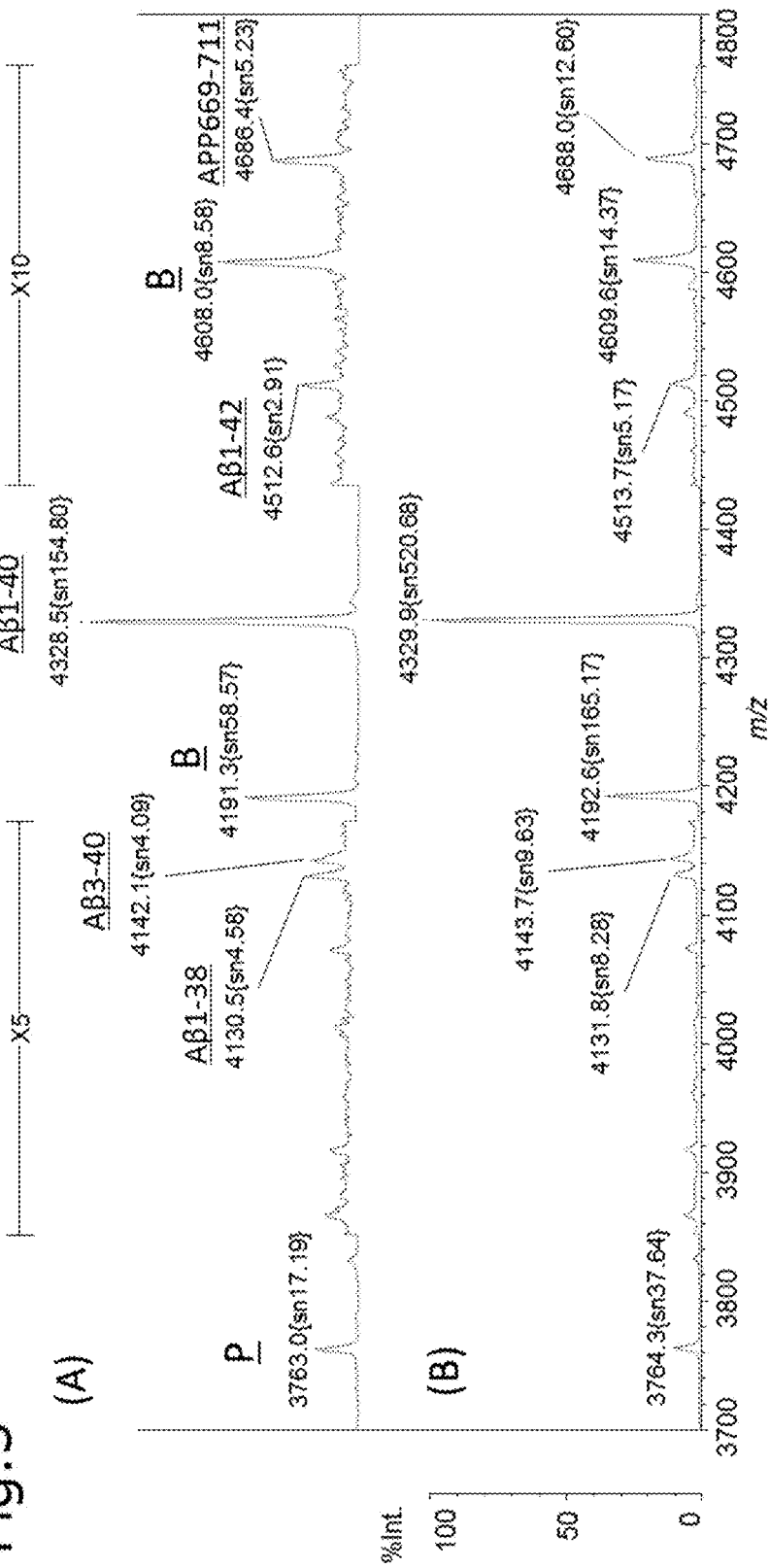
FIG. 5 shows the results of measurement by MALDI-MS after the Consecutive Immunoprecipitation (cIP) operation with the use of the anti-Aβ IgG-immobilizing beads targeting Aβ-related peptides in a plasma sample in Experimental Example 8, in which (A) shows the result of measurement by MALDI-MS when the first IP eluent amount was 45 μL, and the second IP reaction solution amount was 100 μL, and (B) shows the result of measurement by MALDI-MS when the first IP eluent amount was 15 μL, and the second IP reaction solution amount was 30 μL.

That is, FIG. 5 shows the results of measurement by MALDI-MS after the consecutive immunoprecipitation cIP operation with the use of the anti-Aβ IgG-immobilizing beads targeting Aβ-related peptides in a plasma sample in Experimental Example 8, in which (A) shows the result of measurement by MALDI-MS when the first IP eluent amount was 45 μL, and the second IP reaction solution amount was 100 μL, and (B) shows the result of measurement by MALDI-MS when the first IP eluent amount was 15 μL, and the second IP reaction solution amount was 30 μL. In FIG. 5, "P" indicates peaks of impurity substances derived from plasma, and "B" indicates peaks of impurity substances derived from antibody beads.

As shown in FIG. 5, S/N of all detected peptides (Aβ1-8, Aβ3-40, Aβ1-40, Aβ1-42, APP669-711) increased comparatively when the second IP reaction solution amount was 30 μL. This indicated that detection by MALDI-MS with high sensitivity is possible by reducing the second IP reaction solution amount.

Experimental Example 9: Reaction Condition of cIP Effective for High-Sensitive Measurement of MALDI-MS: Number of Antibody Beads in First IP In the conventional immunoprecipitation (IP), the amount of antigen to be bound increases as the number of the antibody-immobilizing beads increases, but the effect of improving the sensitivity in MALDI-MS is not expected because the impurity substances that are non-specifically adsorbed to the antibody-immobilizing beads increase as well. However, in the cIP, even when impurity substances increase due to increased number of the antibody-immobilizing beads in the first IP, the impurities can be removed in the second IP, so that the effect of improving the sensitivity in MALDI-MS by increasing the number of antibody-immobilizing beads can be expected.

Thus, cIP was conducted according to the consecutive immunoprecipitation cIP in Experimental Example 3 with the use of: the anti-Aβ IgG-immobilizing beads; four different quantities of beads (approximately $1 \times 10^7$ beads, $2 \times 10^7$ beads, $4 \times 10^7$ beads, $8 \times 10^7$ beads) for the anti-Aβ IgG-immobilizing beads used in the first IP; and the anti-Aβ IgG-immobilizing beads in the second IP in the number of approximately $1 \times 10^7$ beads, while the first IP eluent amount was 15 μL, and the liquid amount of the first purified solution was 30 μL, and thus a second purified solution was obtained, and the second purified solution was measured by MALDI-MS. These results are shown in FIG. 6.

Figure 6:
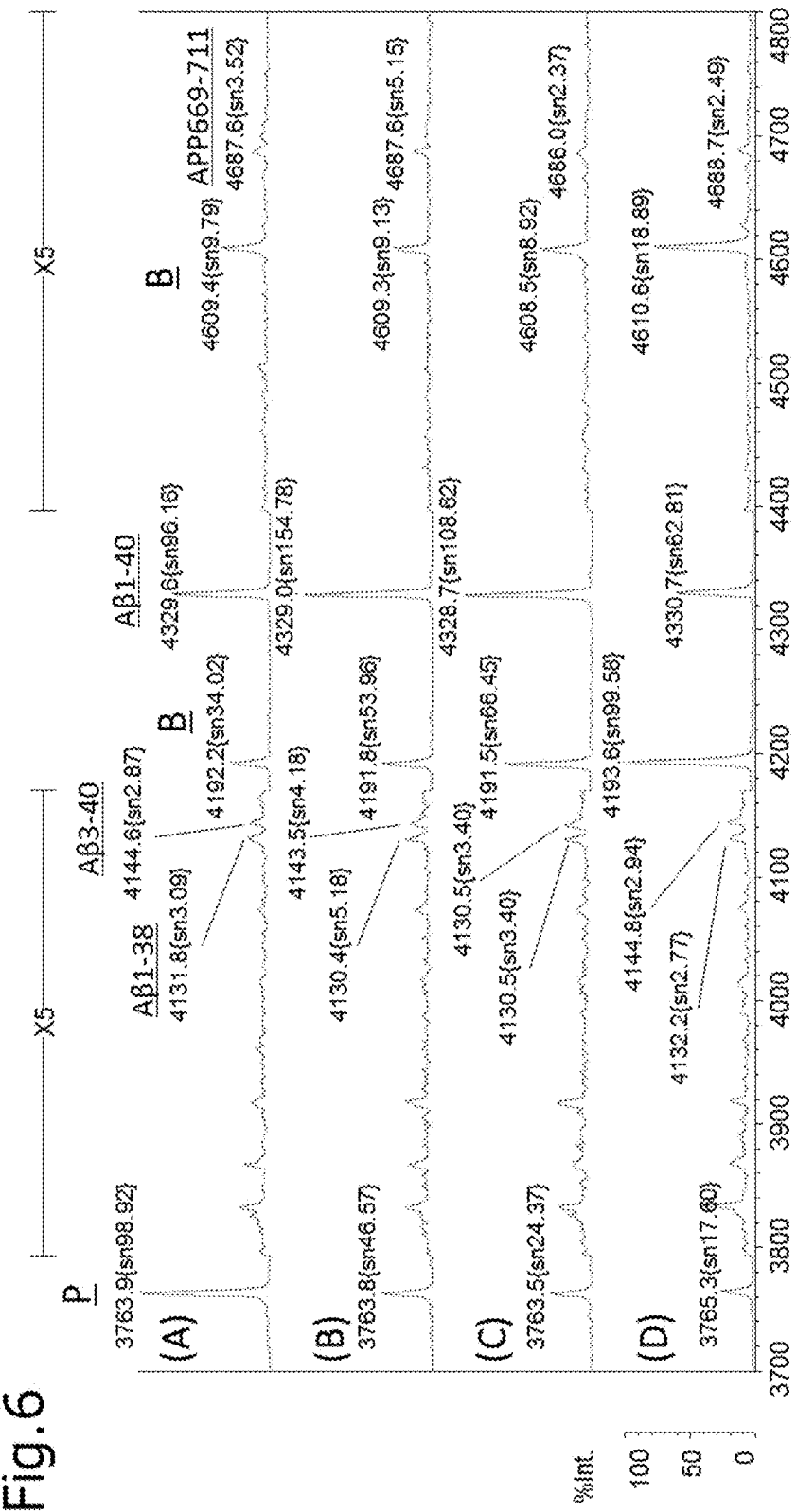
FIG. 6 shows the results of measurement by MALDI-MS after the consecutive immunoprecipitation cIP operation with the use of the anti-Aβ IgG-immobilizing beads targeting Aβ-related peptides in a plasma sample in Experimental Example 9, in which (A) shows the result for the number of the anti-Aβ IgG-immobilizing beads in the first IP: approximately $8 \times 10^7$ beads, (B) shows the result for the number of the anti-Aβ IgG-immobilizing beads in the first IP: approximately $4 \times 10^7$ beads, (C) shows the result for the number of the anti-Aβ IgG-immobilizing beads in the first IP: approximately $2 \times 10^7$ beads, and (D) shows the result for the number of the anti-Aβ IgG-immobilizing beads in the first IP: approximately $1 \times 10^7$ beads, and in (A) to (D), the number of the anti-Aβ IgG-immobilizing beads in the second IP was approximately $1 \times 10^7$ beads.

That is, FIG. 6 shows the results of measurement by MALDI-MS after the consecutive immunoprecipitation cIP operation with the use of the anti-Aβ IgG-immobilizing beads targeting Aβ-related peptides in a plasma sample in Experimental Example 9, in which (A) shows the result for the number of the anti-Aβ IgG-immobilizing beads in the first IP: approximately $8 \times 10^7$ beads, (B) shows the result for the number of the anti-Aβ IgG-immobilizing beads in the first IP: approximately $4 \times 10^7$ beads, (C) shows the result for the number of the anti-Aβ IgG-immobilizing beads in the first IP: approximately $2 \times 10^7$ beads, and (D) shows the result for the number of the anti-Aβ IgG-immobilizing beads in the first IP: approximately $1 \times 10^7$ beads. In FIG. 6, "P" indicates peaks of impurity substances derived from plasma, and "B" indicates peaks of impurity substances derived from antibody beads.

As shown in FIG. 6, as the number of the anti-Aβ IgG-immobilizing beads in the first IP increased from approximately $1 \times 10^7$ beads to approximately $4 \times 10^7$ beads, S/N also increased for all detected peptides (Aβ1-38, Aβ3-40, Aβ1-40, APP669-711). In the number of beads of approximately $8 \times 10^7$ beads, S/N was slightly deteriorated. This is attributable to the fact that elution efficiency was insufficient for the increased number of beads, and/or to the fact that impurity substances that had not been removed even in the second IP caused ion suppression. Thus, the cIP can obtain the sensitivity improving effect, which could not be obtained by the conventional IP, with an increase in the number of antibody beads.

Experimental Example 10: Reaction Condition of cIP Effective for High-Sensitive Measurement of MALDI-MS: Number of Antibody Beads in Second IP According to the consecutive immunoprecipitation cIP in Experimental Example 3, an optimum number of antibody beads in the second IP was examined by using the anti-Aβ

IgG-immobilizing beads. The cIP was conducted with the use of: the anti-Aβ IgG-immobilizing beads used in the first IP in the number of approximately 4×10⁷ beads; and four different quantities of beads (approximately 0.5×10⁷ beads, 1×10⁷ beads, 2×10⁷ beads, 4×10⁷ beads) for the anti-Aβ IgG-immobilizing beads used in the second IP, while the first IP eluent amount was 15 µL, and the liquid amount of the first purified solution was 30 µL, and thus a second purified solution was obtained, and the second purified solution was measured by MALDI-MS. These results are shown in FIG. 7.

Figure 7:
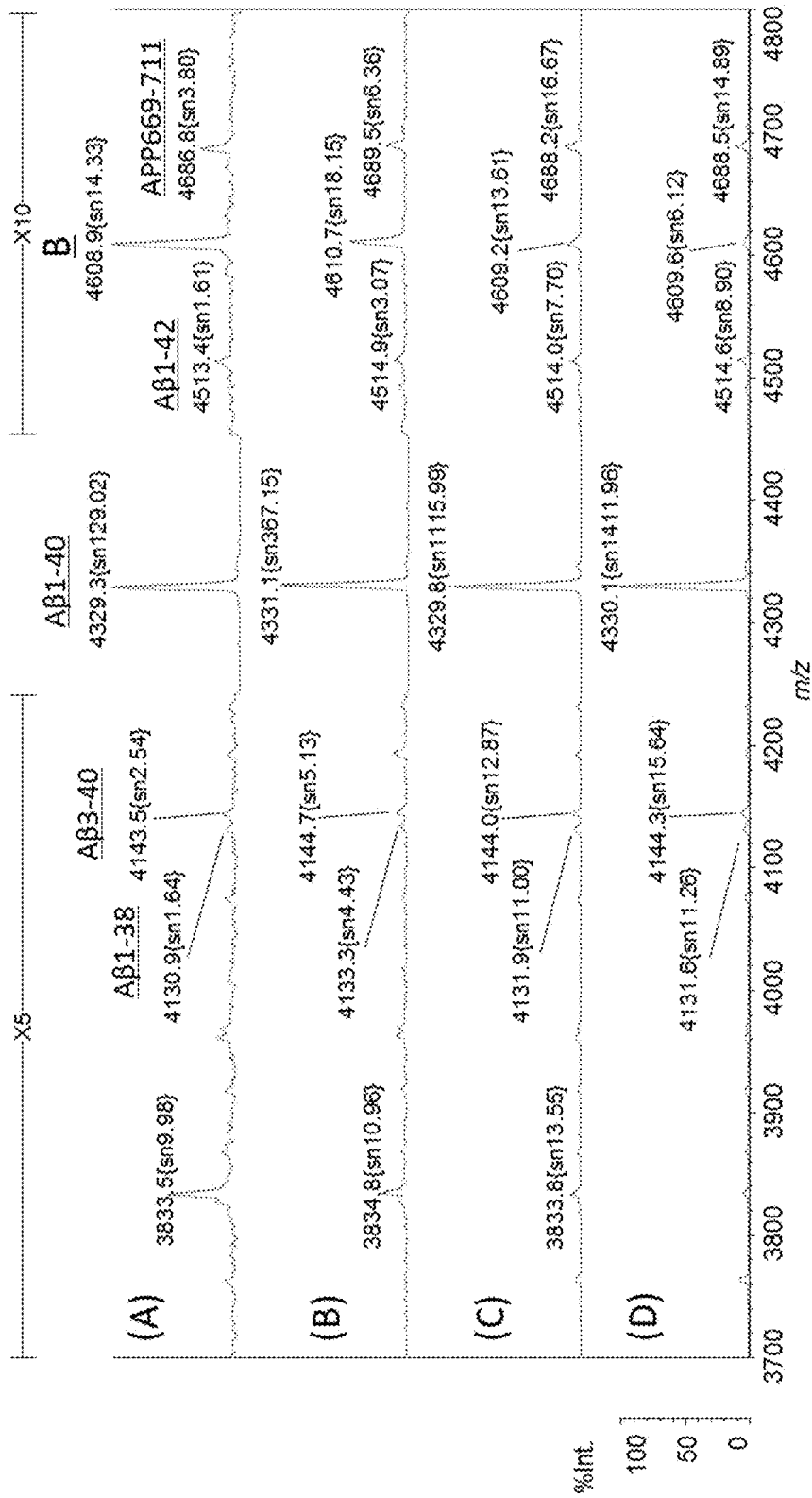
FIG. 7 shows the results of measurement by MALDI-MS after the consecutive immunoprecipitation cIP operation with the use of the anti-Aβ IgG-immobilizing beads targeting Aβ-related peptides in a plasma sample in Experimental Example 10, in which (A) shows the result for the number of the anti-Aβ IgG-immobilizing beads in the second IP: approximately $4 \times 10^7$ beads, (B) shows the result for the number of the anti-Aβ IgG-immobilizing beads in the second IP: approximately $2 \times 10^7$ beads, (C) shows the result for the number of the anti-Aβ IgG-immobilizing beads in the second IP: approximately $1 \times 10^7$ beads, and (D) shows the result for the number of the anti-Aβ IgG-immobilizing beads in the second IP: approximately $0.5 \times 10^7$ beads, and in (A) to (D), the number of the anti-Aβ IgG-immobilizing beads in the first IP was approximately $4 \times 10^7$ beads.

That is, FIG. 7 shows the results of measurement by MALDI-MS after the consecutive immunoprecipitation cIP operation with the use of anti-Aβ IgG-immobilizing beads targeting Aβ-related peptides in a plasma sample in Experimental Example 10, in which (A) shows the result for the number of the anti-Aβ IgG-immobilizing beads in the second IP: approximately 4×10⁷ beads, (B) shows the result for the number of the anti-Aβ IgG-immobilizing beads in the second IP: approximately 2×10⁷ beads, (C) shows the result for the number of the anti-Aβ IgG-immobilizing beads in the second IP: approximately 1×10⁷ beads, and (D) shows the result for the number of the anti-Aβ IgG-immobilizing beads in the second IP: approximately 0.5×10⁷ beads. In FIG. 7, "B" indicates peaks of impurity substances derived from antibody beads.

FIG. 7 revealed that S/N increases as the number of the anti-Aβ IgG-immobilizing beads in the second IP decreases for all detected Aβ-related peptides (Aβ1-38, Aβ3-40, Aβ1-40, APP669-711). This is attributable to the fact that the amount of impurity substances derived from antibody beads eluted from the antibody beads reduces as the number of antibody beads in the second IP increases, and thus the influence by ion suppression reduces to increase the S/N.

According to the present invention, by conducting affinity purification twice consecutively, the impurity substances that have not been excluded only with the first affinity purification can be further reduced with the second affinity purification. Therefore, it is possible to prevent suppression of ionization of polypeptides by the impurity substances, and it becomes possible to measure even trace polypeptides in a biological sample by mass spectrometry. It is also possible to further reduce the impurity substances by conducting the affinity purification three or more times. However, as shown herein, the effect on mass spectrometry by conducting affinity purification twice is verified, and a demerit of reducing the target polypeptides arises by conducting the affinity purification three or more times.

Aβ1-38 (SEQ ID NO: 1):
DAEFRHDSGYEVHHQKLVFFAEDVGSNKGAIIGLMVGG

Aβ3-40 (SEQ ID NO: 2):
EFRHDSGYEVHHQKLVFFAEDVGSNKGAIIGLMVGGVV

Aβ1-40 (SEQ ID NO: 3):
DAEFRHDSGYEVHHQKLVFFAEDVGSNKGAIIGLMVGGVV

Aβ1-42 (SEQ ID NO: 4):
DAEFRHDSGYEVHHQKLVFFAEDVGSNKGAIIGLMVGGVVIA

APP669-711 (SEQ ID NO: 5):
VKMDAEFRHDSGYEVHHQKLVFFAEDVGSNKGAIIGLMVGGVV

The invention claimed is:

1. A method for measuring a target Aβ-related peptide in a biological sample, the method comprising:
- a first reaction step of bringing a liquid containing a biological sample into contact with a first antibody-immobilizing carrier that includes a carrier and an antibody bound to the carrier and having an antigen binding site capable of recognizing a target Aβ-related peptide, to bind the target Aβ-related peptide in the biological sample with the first antibody-immobilizing carrier;
- a first washing step of washing the first antibody-immobilizing carrier to which the target Aβ-related peptide is bound;
- a first eluting step of dissociating and eluting the target Aβ-related peptide from the first antibody-immobilizing carrier by using an acidic solution to obtain a first eluate;
- a neutralizing step of making pH of the eluate neutral by adding a neutral buffer to the first eluate to obtain a first purified solution with neutralized pH;
- a second reaction step of bringing the first purified solution into contact with a second antibody-immobilizing carrier that includes a carrier and an antibody bound to the carrier and having an antigen binding site capable of recognizing the target Aβ-related peptide, to bind the target Aβ-related peptide in the first purified solution with the second antibody-immobilizing carrier, wherein the antibody in the second antibody-immobilizing carrier is the same as the antibody in the first antibody-immobilizing carrier;
- a second washing step of washing the second antibody-immobilizing carrier to which the target Aβ-related peptide is bound;
- a second eluting step of dissociating and eluting the target Aβ-related peptide from the second antibody-immobilizing carrier by using an acidic solution to obtain a second purified solution; and
- a step of detecting the target Aβ-related peptide in the second purified solution by mass spectrometry,
- wherein a liquid amount of the first purified solution subject to the second reaction step is 0.1 to 50% by volume on the basis of a liquid amount of the biological sample liquid subjected to the first reaction step, and
- an amount of the second antibody-immobilizing carrier in the second reaction step is 1 to 50% by surface area of the carrier on the basis of an amount of the first antibody-immobilizing carrier in the first reaction step.

2. The method according to claim 1, wherein in the first eluting step, the acidic solution is an acidic solution containing a surfactant.

3. The method according to claim 1, wherein in the second eluting step, the acidic solution is an acidic solution containing an organic solvent.

4. The method according to claim 3, wherein the organic solvent comprises at least one selected from the group consisting of acetonitrile, acetone, methanol, ethanol, isopropanol, and chloroform.

5. The method according to claim 3, wherein a concentration of the organic solvent in the acidic aqueous solution is 10 to 90% (v/v).

6. The method according to claim 1, wherein the biological sample is whole blood.

7. The method according to claim 1, wherein in the mass spectrometry, a matrix-assisted laser desorption/ionization mass spectrometer is used.

8. The method according to claim 7, in the matrix-assisted laser desorption/ionization mass spectrometer, a matrix comprising at least one selected from the group consisting of α-cyano-4-hydroxycinnamic acid (CHCA), 2,5-dihydroxybenzoic acid (2,5-DHB), sinapic acid, and 3-aminoquinoline (3-AQ) is used.

9. The method according to claim 7, in the matrix-assisted laser desorption/ionization mass spectrometer, a concentration of the matrix is 0.1 to 50 mg/m L.

10. The method according to claim 7, in the matrix-assisted laser desorption/ionization mass spectrometer, a matrix solvent comprising at least one selected from the group consisting of acetonitrile (ACN), trifluoroacetic acid (TFA), methanol, ethanol and water is used.

11. The method according to claim 7, wherein in the matrix-assisted laser desorption/ionization mass spectrometer, a matrix additive is used, wherein the matrix additive comprises at least one selected from the group consisting of phosphonic acid, methylphosphonic acid, phenylphosphonic acid, 1-naphthylmethylphosphonic acid, methylenediphosphonic acid (MDPNA), ethylenediphosphonic acid, ethane-1-hydroxy-1,1-diphosphonic acid, nitrilotriphosphonic acid, and ethylenediaminetetraphosphonic acid.

12. The method according to claim 7, wherein in the matrix-assisted laser desorption/ionization mass spectrometer, a matrix additive prepared as a solution of 0.1 to 10 w/v % in water or in a matrix solvent is used.

13. The method according to claim 1, wherein the biological sample is plasma.

14. The method according to claim 1, wherein the biological sample is serum.

15. The method according to claim 1, wherein at least one of the carriers in the first antibody-immobilizing carrier and in the second antibody-immobilizing carrier comprises at least one material selected from the group consisting of agarose, dextran, silica gel, polyacrylamide, polystyrene, polyethylene, polypropylene, polyester, polyacrylonitrile, (meth)acrylicacid polymer, fluororesin, metal complex resin, glass, metal, and magnetic substance.

16. The method according to claim 1, wherein the antibodies are IgG antibodies.

17. The method according to claim 1, wherein the target Aβ-related peptide is Aβ1-38.

18. The method according to claim 1, wherein the target Aβ-related peptide is Aβ3-40.

19. The method according to claim 1, wherein the target Aβ-related peptide is Aβ1-40.

20. The method according to claim 1, wherein the target Aβ-related peptide is APP669-711.

21. The method according to claim 1, wherein at least one of the antibodies in the first antibody-immobilizing carrier and in the second antibody-immobilizing carrier is bound to the carrier via a spacer.

\* \* \* \* \*